United States Patent [19]
Chauvin et al.

[11] 4,320,243
[45] Mar. 16, 1982

[54] PROCESS FOR PRODUCING PROPENE AND/OR BUTENE OLIGOMERS

[75] Inventors: Yves Chauvin, Le Pecq; Jean Gaillard, Lyons; Gérard Léger, Saint Genis les Ollieres; Hugo Van Landeghem, Oytier Saint Oblas, all of France

[73] Assignee: Institut Francais du Petrole, Rueil-Malmaison, France

[21] Appl. No.: 24,335

[22] Filed: Mar. 27, 1979

[30] Foreign Application Priority Data

Mar. 28, 1978 [FR] France ............................. 78 09197

[51] Int. Cl.³ ............................................. C07C 2/02
[52] U.S. Cl. ................................... 585/521; 585/428; 585/429; 585/502; 585/512; 585/531; 585/532; 585/950

[58] Field of Search ............... 585/502, 512, 517, 521, 585/532, 428, 429, 950, 531

[56] References Cited

U.S. PATENT DOCUMENTS 2,791,549  5/1957  Jahnig .................................. 585/950
3,067,268  12/1962  Dunlop et al. ....................... 585/950

FOREIGN PATENT DOCUMENTS 1233557  5/1971  United Kingdom .

Primary Examiner—Curtis R. Davis
Attorney, Agent, or Firm—Millen & White

[57] ABSTRACT

At least one of propene and butene is oligomerized, preferably dimerized, in an elongate cylindrical reaction zone. A recycle flow and the fresh feed charge are injected tangentially into said reaction zone. The catalyst preferably comprises a nickel compound and a hydrocarbyl aluminum halide.

10 Claims, 4 Drawing Figures

PROCESS FOR PRODUCING PROPENE AND/OR BUTENE OLIGOMERS

This invention relates to a process for producing oligomers, particularly propene and/or butene dimers or co-dimers, for example 1-butene or 2-butene dimers or co-dimers, in the liquid phase. Resultant oligomers are liquid and soluble in the hydrocarbon reaction medium.

A process is known, according to which propene and/or butene are oligomerized in the liquid phase, in the presence of a catalyst, for example, a catalyst formed by reacting a nickel compound with a hydrocarbyl aluminum halide.

This process is conventionally carried out in batch, i.e. in a discontinuous manner. A continuous mode of operation is however disclosed, for example, in the French Pat. No. 1 591 577 or the U.S. Pat. No. 3,511,891. When operating in continuous manner, the contact time of the olefin with the catalyst is usually 2 to 6 hours, corresponding to liquid olefin flow rates of about 0.15 to 0.5 liter per liter of reaction space. It is however observed after a few hours of operation, that black sticky deposits form on the reactor walls, the weight of which increases with time, and which can obstruct the inlet and outlet ducts for the materials. These deposits appear to form essentially from the catalyst since they have high contents of halogen (chlorine), aluminum and active metal (nickel). Their specific weight is largely higher than that of the reaction liquid phase.

One object of the present invention is to obviate this disadvantage of the prior technique.

The invention relates to a process for producing oligomers, wherein a hydrocarbon liquid feed charge comprising propene and/or butene is contacted with an oligomerization catalyst dispersed in said charge, characterized in that the operation is conducted in at least one elongate, substantially cylindrical reaction zone, at a feed rate of the liquid phase of at least 5 liters per liter of reaction space per hour and at an average residence time of propene and/or butene of 0.5 to 10 hours, by injecting at least a portion of the liquid feed of the fresh and/or recycled reactants in a tangential direction, to thereby give to that feed a circular motion in the reaction zone, which adds to the longitudinal translation motion in said zone.

The operation according to the invention is thus conducted at a hourly feed rate of the hydrocarbon liquid phase of at least 5 liters, for example 10 to 50 and preferably 20 to 40 liters, per liter of reaction space.

In order to obtain, with such feed rates, aa residence time of the olefin of about 0.5 to 10, preferably 1 to 5 hours, the feed charge is diluted with a portion of the discharge from the reaction zone, the dilution rate being advantageously from 10 to 200, preferably 15 to 80 volumes of recycled liquid phase per volume of the fresh feed charge.

According to a preferred embodiment, the reaction is performed in an elongate cylindrical reaction zone, by injecting the recycle flow and preferably also the feed charge in a tangential direction, i.e. a direction which is both non-parallel to the longitudinal axis of the reaction zone and not directed towards said axis. This injection is preferably effected from the side wall of the cylinder and its direction is comprised within the plane perpendicular to the cylinder axis, passing through the injection point, or makes with that plane an angle lower than 45°. That direction or its projection on said plane, makes with the tangent to the cylinder an angle preferably lower than 30°. The liquid phase has thus a circular motion which adds to the translation motion in the cylindrical reaction zone. This double motion has the advantage of resulting in a substantial reduction, if not complete disappearance, of the deposits, and in a more complete utilization of the reaction space by reducing the dead zones.

According to a more preferred embodiment, the tangential injection is effected at at least two distinct levels of the cylinder, i.e. at least two points spaced apart in the direction of the longitudinal axis of the cylinder, for example at the top and in the middle of the reactor. Instead of one single injector at a given level of the cylinder, a plurality of injectors, for example two or three, may be arranged regularly at the periphery of the cylinder, all arranged substantially in the same cross-sectional plane of the latter and oriented in the same direction as the circular flow of the fluids.

It appears that the injection rate of the recycled liquid is of importance. The best results are obtained with injection rates of 1 to 10 meters per second, preferably 2 to 7 meters per second.

FIG. 1 represents a portion of a cylindrical reactor 1 of axis XX'.

FIGS. 2 and 3 represent cross-sections of reactor 1 by a plane perpendicular to the axis XX' and passing through the points A and B located on the wall of the cylinder.

Figure 1:
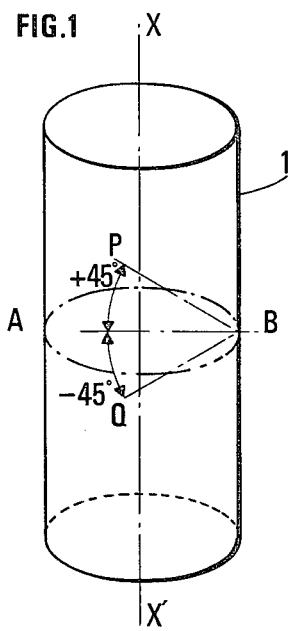
FIGS. 1 to 3 illustrate various embodiments of the invention.
Figure 2:
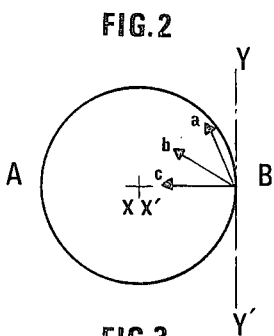

B (FIG. 1) is an injection point for the charge and recycle feed. This injection is effected into the cylinder within angle PBQ in any direction, except direction $\overline{BA}$ or any other direction crossing the axis XX'. The directions $\overline{Ba}$ and $\overline{Bb}$ are permitted (FIG. 2), and not the direction $\overline{Bc}$ crossing the axis XX'. It is clear that it is advantageous to select a direction as remote as possible from direction $\overline{Bc}$, so that the angle with the tangent YY' be as low as possible. $\overline{Ba}$ is thus preferred to $\overline{Bb}$.

Figure 3:
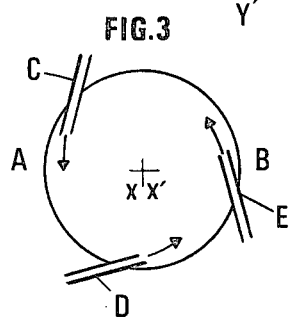

Three injection nozzles C, D, E are shown on FIG. 3. They are in the plane of FIG. 3, although they can be inclined to that plane, the inclination angle being preferably lower than 45°.

Figure 4:
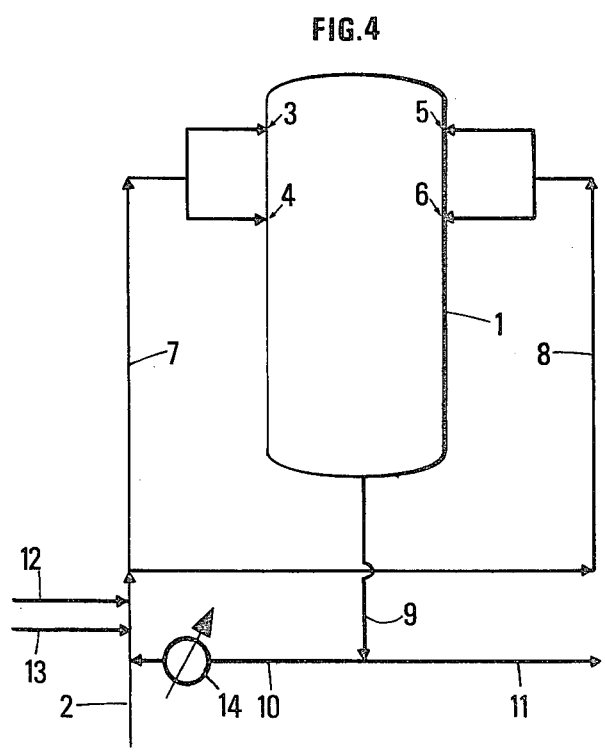
FIG. 4 is an overall view of the plant.

According to FIG. 4, the $C_3$ and/or $C_4$ olefinic cut is admitted through duct 2 into reactor 1, while passing through branches 7 and 8 and tangential injectors 3 to 6. The effluent is discharged through duct 9 and divided into a recycle flow (duct 10) and a production flow (duct 11) which is supplied to a further stage of similar type or to a zone of known type for final treatment, to separate the oligomers, particularly the dimers. This final treatment may produce, for example, the catalyst destruction, for example by means of water or sodium hydroxide, and optional water-washing; when desired, it is terminated with distillation.

The reaction heat may be transferred to an exchanger 14. The two main constituents of the catalyst (a nickel compound and an organoaluminum compound) are fed through ducts 12 and 13. The circulation pumps and other secondary devices, for example heat exchangers, have not been shown for sake of simplicity.

The operating conditions are conventional for reactions of this type, i.e. a preferred temperature of 10° to 70° C. and a sufficient pressure to maintain a liquid phase.

The catalysts to be used according to the invention are well-known in the art and do not necessitate a detailed description.

Examples of catalysts are: nickel dichloride, nickel acetylacetonate, nickel carboxylates, bis-π-allyl nickel compounds, bis-cyclooctadiene nickel, complexes of inorganic nickel salts with organic trivalent phosphorus compounds, for example phosphines, such as the Ni Cl₂, 2-tributyl phosphine complex, alone or preferably associated with one or more compounds comprising a metal-carbon bond, preferably of the formula:

$$Al_2R_nX_{6-n}$$

where n=2, 3 or 4, R is a monovalent hydrocarbon radical or an alkoxy radical and X is a halogen atom. Examples thereof are: phenylaluminum dichloride, ethylaluminum sesquichloride, dibromocyclohexylaluminum and dichloroethylaluminum.

The catalyst or its starting components may be supplied progressively during the reaction, either into the reactor or into the recycle flow. The catalyst is usually employed in such an amount that the ratio: milligratoms Ni/olefin moles is from 0.007:1 to 0.3:1 and preferably from 0.02:1 to 0.1:1, while the amount of aluminum compound is preferably so selected as to provide an atomic Al/Ni ratio from 0.5:1 to 20:1.

Additional compounds may be present, among which complexants such as phosphines.

Inert diluents may be used, for example of the liquid saturated hydrocarbon type.

The invention is not limited to the use of a single reaction stage of the above type. For example from 2 to 6 stages and preferably from 2 to 4 stages may be used, arranged side by side, each of which has its own re-circulation system.

When operating in a plurality of stages, the whole amount of the reactants and catalyst may be fed to the first reactor. Improved results are however obtained by injecting the catalyst stepwise into several stages or into all stages. Again, as concerns co-dimerization, one olefin, for example butene, may be fed at the top and the other olefin, for example propylene, may be fed fractionwise at different levels.

The invention is not intended to be limited to the use of particular dimerization or codimerization catalysts, or to the use of specific proportions of these catalysts, or to the use of specific operating conditions. Other olefins than $C_3$ and $C_4$ olefins can also be used.

EXAMPLE

The apparatus, as shown in FIG. 4, has two pairs of injectors arranged at different levels, the first one at the top, the other one at a one third distance from the top. The injection rate is 7 meters per second. The injection is of the tangential type. The axis of the cylinder is vertical.

The hydrocarbon charge comprises by mole:
propylene: 66%
propane: 34%

The operation is conducted at 40° C. under a pressure of 20 kg/cm². Each volume of the fresh charge is diluted with 45 volumes of recycled effluent while discharging approximately the same weight of effluent as the weight of the fresh charge, to recover the oligomers. The hourly flow rate of the liquid phase (charge+recycle) is 25 volumes per volume of reaction space, defined as the volume of the reactor plus the volume of the recycle circuit. Under these conditions, the average residence time for propylene is about 2.7 hours. 0.3 kg of dichloroethylaluminum and 0.1 kg of a nickel octanoate solution (10% b.w. of nickel) are injected, per each metric ton of fresh hydrocarbon charge.

The outflow is analysed:
propylene: 9% by mole
propane: 50%
hexenes: 36%
nonenes: 3.5%
dodecenes: 0.5%

It is found that 90% of propylene has been converted and the molar oligomer yield, with respect to propylene, is practically quantitative.

After one month of continuous run, no trouble has been observed and no deposit was present on the vertical and horizontal walls, when opening the reactor.

COMPARISON EXAMPLE

The same hydrocarbon charge is treated, in the same conditions as in the above example, except that the liquid feed charge, diluted as above with a portion of the outflow, is admitted at the top of the reactor and along the axis of the reactor, opposite to the outlet line 9.

In these conditions, it is found that the conversion is only 85% in the first days of run and only 78% after one week. Purges have been effected daily from line 9 to remove at each time 0.001 volume of black viscous liquid per each volume of reaction space. After one month of run, the reactor was emptied and 0.05 volume of black sticky material was collected per each volume of reaction space.

What we claim is:
1. A process for producing at least one hydrocarbon-soluble oligomer, while decreasing or suppressing the formation of black sticky catalyst deposit formation on reactor walls, which process comprises:
   (a) feeding a liquid hydrocarbon charge comprising at least one olefinic hydrocarbon selected from propene and the butenes with an oligomerization catalyst dispersed in said charge into at least one elongated, substantially cylindrical reaction zone, at an hourly feed rate of at least 5 liters of said liquid charge per liter of reaction space in said reaction zone and at an average residence time of said olefinic hydrocarbon from 0.5 to 10 hours, said feeding being effected at least partly in a tangential direction, to thereby give to said liquid charge a circular motion in the reaction zone, and said reaction zone being maintained at liquid phase oligomerization conditions of temperature and pressure, said oligomerization catalyst being a material obtained by reacting at least one nickel compound with at least one hydrocarbyl aluminum halide,
   (b) displacing said liquid hydrocarbon charge axially in said reaction zone, thereby adding a translation motion to the circular motion of said charge, and
   (c) discharging a liquid stream from said reaction zone, said discharged stream consisting essentially of the whole unfractionated reaction product and comprising all hydrocarbon-soluble oligomer formed and all unreacted hydrocarbon, said process resulting in decreased or suppressed catalyst deposit formation.

2. A process according to claim 1, wherein the tangential injection is effected from at least two points at the periphery of the cylindrical reaction zone spaced apart at distinct levels of said zone.

3. A process according to claim 1, wherein the hourly feed rate of the liquid charge is 20 to 40 liters per liter of reaction space.

4. A process according to claim 1,
wherein the liquid charge is injected tangentially at a rate of 1 to 10 meters per second.

5. A process according to claim 1,
which is operated in at least two successive reaction zones.

6. A process according to claim 5, wherein the catalyst is introduced portionwise in each successive reaction zone.

7. A process according to claim 1, wherein one portion of the unfractionated liquid stream discharged from the reaction zone is recycled to the reaction zone to constitute one part of the liquid charge fed to said reaction zone, said portion amounting to 10–200 volumes per volume of freshly fed liquid charge.

8. A process according to claim 1, wherein said catalyst is fed in an amount providing 0.007–0.3 milligram-atoms of nickel per mol. of olefin, and the atomic ratio of aluminum to nickel is from 0.5:1 to 20:1.

9. A process according to claim 7, wherein the oligomerization catalyst comprises a nickel compound, and the liquid charge is injected at a rate of 2 to 8 meters per second.

10. A process according to claim 1, wherein the liquid hydrocarbon charge comprises propylene and propane, and the catalyst consists essentially of dichloroethyl aluminum and nickel octanoate.

* * * * *